United States Patent [19]

Ford et al.

[11] 4,316,840

[45] Feb. 23, 1982

[54] REFORMING LINEAR POLYAMINES

[75] Inventors: Michael E. Ford, Trexlertown; Thomas A. Johnson, Orefield, both of Pa.

[73] Assignee: Air Products and Chemicals, Inc., Allentown, Pa.

[21] Appl. No.: 210,209

[22] Filed: Nov. 25, 1980

[51] Int. Cl.$^3$ .................. C07C 85/00; C07C 85/20; C07D 241/04; C07D 295/12
[52] U.S. Cl. .................. 260/239 BC; 544/358; 544/402; 564/511; 564/512
[58] Field of Search ............... 564/512, 511; 544/358, 544/402; 260/239 BC

[56] References Cited

U.S. PATENT DOCUMENTS

| T945,004 | 4/1976 | Valaitis et al. | 564/511 |
| 3,217,028 | 11/1965 | Vertnik | 564/511 |
| 3,714,259 | 1/1973 | Lichtenwalter et al. | 260/583 P |
| 3,751,474 | 8/1973 | Phillips et al. | 260/583 P |
| 4,036,881 | 7/1977 | Brennan et al. | 260/583 P |
| 4,044,053 | 8/1977 | Brennan et al. | 260/583 P |

OTHER PUBLICATIONS

Genty, "Chemical Abstracts," vol. 72, Ab. No. 113505y (1970).

Primary Examiner—John Doll
Attorney, Agent, or Firm—Russell L. Brewer; E. Eugene Innis; James C. Simmons

[57] ABSTRACT

Process for production of polyalkylene polyamines, preferably non-cyclic polyalkylene polyamines, by reforming of other polyalkylene polyamines. The reforming process is effected by reacting the polyalkylene polyamine starting material in the presence of a metal nitrate or sulfate, preferably a sulfate, catalyst at elevated temperature and pressure and in the presence of sufficient water and sufficient catalyst, for a reaction period and under reaction conditions otherwise adapted to bring about the desired reforming reaction.

9 Claims, No Drawings

REFORMING LINEAR POLYAMINES

TECHNICAL FIELD

This invention pertains to the catalyzed reforming of ethylene diamine or polyalkylene polyamines to other polyalkylene polyamines.

BACKGROUND OF PRIOR ART

Various processes and catalysts have been disclosed for producing polyalkylene polyamines, including those disclosed in the patents listed below. These listed U.S. patents have been considered with reference to patentability of the invention disclosed and claimed herein. However, they are not considered sufficiently relevant for separate comment.
- U.S. Pat. No. 4,103,087—Brennan
- U.S. Pat. No. 4,123,462—Best
- U.S. Pat. No. 4,061,633—Blyakhman et al
- U.S. Pat. No. 3,270,059—Winderl et al
- U.S. Pat. No. 3,037,023—Moss et al
- U.S. Pat. No. 3,565,957—Mirviss et al
- U.S. Pat. No. 3,281,470—Vertnik
- U.S. Pat. No. 2,519,803—Weber et al
- U.S. Pat. No. 3,255,248—Suesengoth et al
- U.S. Pat. No. 3,427,356—Baer et al With regard to the preparation of higher polyalkylene polyamines by reaction of lower polyalkylene polyamines, British Pat. No. 1,500,220 of the Texaco Development Corporation is of specific interest. According to that patent, predominantly non-cyclic polyamines are formed by reaction of lower polyalkylene polyamines with alkanol amines under elevated temperature and pressure conditions, with a phosphorus-containing catalyst. Among the suitable catalysts are "acidic metal phosphates [including] boron phosphate, ferric phosphate, and aluminum phosphate", (Col. 3, lines 27–29). That patent further teaches, and Examples II and III thereof demonstrate, that the process there taught requires "an alkylating material such as an ethanolamine compound in the process of the invention", (Col. 5, lines 55–59).

With this background in mind, it is the general object of the present invention to provide a practical and economical process for producing various polyalkylene polyamines.

BRIEF SUMMARY OF INVENTION

In accordance with the process of the present invention, various polyalkylene polyamines may be produced by a reforming reaction, by contacting another polyalkylene polyamine or ethylene diamine starting material with water, in the presence of a metal sulfate or nitrate catalyst, at elevated temperature and pressure, the temperature, pressure, catalyst, catalyst and water amounts, and time of reaction being adapted to permit the polyalkylene polyamine starting material to be reformed into some other polyalkylene polyamine.

The preferred starting materials, for producing polyalkylene polyamines, are ethylene-diamine and homologues thereof, particularly including diethylenetriamine and triethylenetetramine.

Various metal sulfates and nitrates are effective in the present invention. Beryllium and ammonium sulfates and beryllium, iron and aluminum nitrates, in particular, are known to be effective. In general, the sulfates are used in the preferred embodiments of the present invention. Other metal sulfates which may be used are the sulfates of lithium, sodium, potassium, and other metals of group IA of the periodic table; magnesium, calcium, and other metals of group IIA of the periodic table; and zinc, zirconium, antimony, iron and tin (valence states II and IV of both iron and tin). Other nitrates which may be used are the nitrates of lithium, sodium, potassium, and other metals of group IA of the periodic table; magnesium, calcium, and other metals of group IIA of the periodic table; and zinc, zirconium, antimony, iron and tin (valence states II and III of iron and II and IV of tin).

In general, the reaction time is on the order of 0.5 to 5 hours (preferably 1–4 hours), the reaction temperature range is 200°–400° C. (preferably 225°–350° C.), the proportion of water present, in weight percent based on the amount of polyamine starting material, is 3–20%, and the amount of catalyst present, in mol percent based on amount of starting material present, is 2–20%, preferably 3–10% (the catalyst amount being recited for a batch process; in a continuous process, contact time may be selected to produce effectively the same degree of catalyzation, a factor which would have to be determined experimentally for the particular process involved).

BRIEF DESCRIPTION OF THE INVENTION

For a better understanding of this invention, reference should be made to the detailed description of experiments which follows. In general, the results indicated for these experiments demonstrate that the reformation of ethylene diamine or polyalkylene polyamines by sulfate and nitrate catalysts, in accordance with the process of the present invention, may vary significantly, as to degree of conversion and as to the distribution of products upon conversion.

In general, the metal sulfate catalysts are preferred in that they appear to produce greater yields than corresponding nitrate catalysts. Moreover, the possible explosive reactivity of nitrate and amines renders nitrate catalysts less practical than sulfate catalysts.

With some exceptions, greater conversions are noted with increasing temperature, at least within the preferred temperature range for the process of the present invention. The same is true with respect to higher concentrations of catalysts and water in the reaction media. As the experimental data listed below indicates, the omission of water significantly impairs the reformation reaction to the point where it is of doubtful utility. Even though some minor amount of reformation may be produced with water alone, in the absence of catalyst, it is apparent that both catalyst and water in amounts adapted to produce the desired reaction are required in each case.

The description of these experiments and the results thereof are set forth below.

EXPERIMENTS 1–4—REFORMING EDA WITH METAL SULFATES AT 300° C.

Experiment 1

A mixture of ethylenediamine (390 mg; $6.5 \times 10^{-3}$ mol) and beryllium sulfate (60 mg; $3.25 \times 10^{-4}$ mol, 5 mol %, based on ethylenediamine) was placed in a two milliliter reactor and heated to 300° C. with agitation for two hours. Cooling and glc analysis indicated that primarily N-(2-aminoethyl)piperazine had been formed and conversion in general was low, particularly with respect to non-cyclic products (see Table I).

Experiment 2

The procedure of Experiment 1 was repeated with inclusion of water (52 mg; 2.92×10⁻⁴ mol, 13.3 weight %, based on ethylenediamine). Glc analysis of the cooled reaction mixture indicated that substantial conversion to polyamines had occurred (see Table I).

Experiment 3

A mixture of ethylenediamine (390 mg; 6.5×10⁻³ mol) and anhydrous ammonium sulfate (45 mg; 3.4×10⁻⁴, 5.2 mol %, based on ethylenediamine) was placed in a two milliliter reactor and heated at 300° C. for 2 hours. Cooling and glc analysis indicated that some N-(2-aminoethyl)piperazine had been formed (see Table I) but conversion in general was low, particularly with respect to non-cyclic products.

Experiment 4

The procedure of Experiment 3 was repeated with inclusion of water (52 mg; 2.92×10⁻⁴ mol, 13.3 weight %, based on ethylenediamine). Glc analysis of the cooled reaction mixture indicated that substantial converson to polyamines had occurred (see Table I).

These experiments demonstrate the beneficial effect of inclusion of water on polyamines reforming by sulfate salt catalysis.

2 hours. Cooling and glc analysis indicated that esssentially no reaction had occurred (see Table II).

Experiment 6

The procedure of Experiment 5 was repeated with inclusion of additional water (52 mg; 2.92×10⁻³ mol, 13.3 weight %, based on ethylenediamine). The total water incorporation from beryllium nitrate (4.5 weight %) and added water (13.3 weight %) was 17.8 weight %, based on ethylenediamine. Glc analysis of the cooled reaction mixture indicated that some conversion to cyclic polyamines had occurred (see Table II).

Experiment 7

A mixture of ethylenediamine (390 mg; 6.5×10⁻³ mol) and ferric nitrate (65 mg; 1.625×10⁻⁴ mol, 2.5 mol % based on ethylenediamine) was placed in a two milliliter reactor. The iron nitrate contained water (26 mg; 1.44×10⁻³ mol, 6.6 weight %, based on ethylenediamine). This mixture was heated at 300° C. with agitation for 2 hours. Cooling and glc analysis indicated that some cyclic triethylenetriamines had been formed (see Table II).

Experiment 8

The procedure of Experiment 7 was repeated with inclusion of additional water (52 mg; 2.92×10⁻³ mol, 13.3 weight %, based on ethylenediamine). The total water incorporation from ferric nitrate (6.6 weight %) and added water (13.3 weight %) was 19.9 weight %, based on ethylenediamine. Glc analysis of the cooled reaction mixture indicated that substantial conversion to cyclic polyamines has occurred (see Table II).

These experiments illustrate the effect of added water in promoting reforming of polyamines by nitrate catalysts.

TABLE I

Reforming Ethylenediamine With Metal Sulfates At 300° C.[a]

| Ex. | Catalyst Level (mol %) | Water (weight %) | EDA[b] | PIP[c] | AEP[d] | DETA[e] | TETA(L)[f] | TETA(C)[g] | TEPA(L)[h] | TEPA(C)[i] | NC[j] |
|---|---|---|---|---|---|---|---|---|---|---|---|
| 1 | 5.0 | 0.0 | * | 0.00 | 3.19 | 0.00 | 0.00 | 0.00 | 0.00 | 0.29 | 0 |
| 2 | 5.0 | 13.3 | * | 5.58 | 6.12 | 2.10 | 0.46 | 7.01 | 0.00 | 0.75 | 12 |
| 3 | 5.0 | 0.0 | * | 0.00 | 2.30 | 0.00 | 0.00 | 0.00 | 0.00 | 0.00 | 0 |
| 4 | 5.0 | 13.3 | * | 0.11 | 4.34 | 1.59 | 0.00 | 0.44 | 0.76 | 0.00 | 32 |

[a]Weight percent of components in product on feedstock-free basis. Catalyst and water incorporations are based on polyamine feedstock. Two hour reaction time, all cases.
[b]Ethylenediamine
[c]Piperazine
[d]Aminoethylpiperazine
[e]Diethylenetriamine
[f]Triethylenetetramine (linear isomers)
[g]Triethylenetetramine (cyclic isomers)
[h]Tetraethylenepentamine (linear isomers)
[i]Tetraethylenepentamine (cyclic isomers)
[j]Weight percent of non-cyclic products
*feedstock

EXPERIMENTS 5-8—REFORMING EDA WITH NITRATE SALTS AT 300° C.

Experiment 5

A mixture of ethylenediamine (390 mg; 6.5×10⁻³ mol) and beryllium nitrate (60 mg; 3.25×10⁻⁴ mol, 5 mol %, based on ethylenediamine) was placed in a two milliliter reactor. The beryllium nitrate also contained water (18 mg; 10⁻³ mol, 4.5 weight %, based on ethylenediamine). This mixture was heated with agitation for

TABLE II

Reforming Ethylenediamine with Nitrate Salts at 300° C.[a]

| Ex. | Catalyst Level (mol %) | Water (weight %) | EDA[b] | PIP[c] | AEP[d] | DETA[e] | TETA(L)[f] | TETA(C)[g] | TEPA(L)[h] | TEPA(C)[i] | NC[j] |
|---|---|---|---|---|---|---|---|---|---|---|---|
| 5 | 5.0 | 4.5 | * | 0.00 | 0.23 | 0.00 | 0.00 | 0.00 | 0.00 | 0.00 | 0 |
| 6 | 5.0 | 17.8 | * | 0.12 | 1.76 | 0.00 | 0.00 | 3.04 | 0.00 | 0.00 | 0 |
| 7 | 2.5 | 6.6 | * | 0.00 | 0.52 | 0.00 | 0.00 | 5.58 | 0.00 | 0.00 | 0 |

TABLE II-continued

| | | | Reforming Ethylenediamine with Nitrate Salts at 300° C.[a] | | | | | | | | |
|---|---|---|---|---|---|---|---|---|---|---|---|
| Ex. | Catalyst Level (mol %) | Water (weight %) | EDA[b] | PIP[c] | AEP[d] | DETA[e] | TETA(L)[f] | TETA(C)[g] | TEPA(L)[h] | TEPA(C)[i] | NC[j] |
| 8 | 2.5 | 19.9 | * | 0.00 | 0.62 | 0.00 | 0.00 | 14.12 | 0.00 | 0.00 | 0 |

[a] Weight percent of components in product on feedstock-free basis. Catalyst and water incorporations are based on polyamine feedstock. Two hour reaction time, all cases.
[b] Ethylenediamine
[c] Piperazine
[d] Aminoethylpiperazine
[e] Diethylenetriamine
[f] Triethylenetetramine (linear isomers)
[g] Triethylenetetramine (cyclic isomers)
[h] Tetraethylenepentamine (linear isomers)
[i] Tetraethylenepentamine (cyclic isomers)
[j] Weight percent of non-cyclic products
*Feedstock

EXPERIMENTS 9–14—REFORMING EDA WITH NITRATE SALTS AT 325° C.

Experiment 9 (for comparison only; no water, no catalyst)

Ethylenediamine (390 mg; $6.5 \times 10^{-3}$ mol) was placed in a two milliliter reactor and heated at 325° C. with agitation for 2 hours. Cooling and glc analysis indicated that no reaction had occurred (see Table III).

Experiment 10 (for comparison only; includes water but no catalyst)

The procedure of Experiment 9 was repeated with inclusion of water (47 mg; $2.6 \times 10^{-3}$, 12 weight %, based on ethylenediamine). Glc analysis of the cooled reaction mixture indicated that a minor amount of reforming had occurred and a mixture of polyamines had been formed (see Table III).

Experiment 11

The procedure of Experiment 5 was repeated at 325° C. Glc analsis of the cooled reaction mixture indicated that substantial conversion to polyamines had occurred (see Table III).

Experiment 12

The procedure of Experiment 11 was repeated at 325° C. with inclusion of water (47 mg; $2.6 \times 10^{-3}$ mol, 12.0 weight %, based on ethylenediamine). Glc analysis of the cooled reaction mixture indicated that some conversion to polyamines had occurred, though less than in Experiment 11 (see Table III).

Experiment 13

The procedure of Experiment 7 was repeated at 325° C. Glc analysis of the cooled reaction mixture indicated that some conversion to polyamines had occurred, though less than in Experiment 7 (see Table III).

Experiment 14

The process of Experiment 8 was repeated at 325° C. with inclusion of water (47 mg; $2.6 \times 10^{-3}$ mol, 12.0 weight %, based on ethylenediamine). Total water, with 66% contributed by catalyst, was 18.6%. Glc analysis of the cooled reaction mixture indicated that some conversion to polyamines had occurred, though less than in Experiment 8 (see Table III).

TABLE III

| | | | Reforming Ethylenediamine With Nitrate Salts at 325° C.[a] | | | | | | | | | |
|---|---|---|---|---|---|---|---|---|---|---|---|---|
| Ex. | Catalyst Level (mol %) | Water (weight %) | MEA[b] | EDA[c] | PIP[d] | AEP[e] | DETA[f] | TETA(L)[g] | TETA(C)[h] | TEPA(L)[i] | TEPA(C)[j] | NC[k] |
| 9 | 0.0 | 0.0 | 0.00 | * | 0.00 | 0.00 | 0.00 | 0.00 | 0.00 | 0.00 | 0.00 | — |
| 10 | 0.0 | 12.0 | 1.08 | * | 0.45 | 0.22 | 0.14 | 0.00 | 0.00 | 0.00 | 0.20 | 58 |
| 11 | 5.0 | 4.5 | 1.99 | * | 0.53 | 0.08 | 0.39 | 0.14 | 5.32 | 0.00 | 0.00 | 30 |
| 12 | 5.0 | 16.5 | 2.87 | * | 0.03 | 0.48 | 0.22 | 0.14 | 2.29 | 0.00 | 0.19 | 52 |
| 13 | 2.5 | 6.7 | 0.15 | * | 0.00 | 0.42 | 0.00 | 0.00 | 2.16 | 0.00 | 0.00 | 6 |
| 14 | 2.5 | 18.6 | 3.50 | * | 0.00 | 0.00 | 0.00 | 0.00 | 2.37 | 0.00 | 0.00 | 60 |

[a] Weight percent of components in product on feedstock-free basis. Catalyst and water incorporations are based on polyamine feedstock. Two hour reaction time, all cases.
[b] Monoethanolamine
[c] Ethylenediamine
[d] Piperazine
[e] Aminoethylpiperazine
[f] Diethylenetriamine
[g] Triethylenetetramine (linear isomers)
[h] Triethylenetetramine (cyclic isomers)
[i] Tetraethylenepentamine (linear isomers)
[j] Tetraethylenepentamine (cyclic isomers)
[k] Weight percent of non-cyclic products, including MEA
*Feedstock

EXPERIMENTS 15–18—REFORMING DETA WITH NITRATE SALTS AT 325° C.

Experiment 15 (for comparison only, no water, no catalyst)

Diethylenetriamine (670 mg; $6.5 \times 10^{-3}$ mol) was placed in a two milliliter reactor and heated at 325° C. with agitation for 2 hours. Cooling and glc analysis of the product indicated that substantially no reaction had occurred (see Table IV).

Experiment 16 (for comparison only, includes water, no catalyst)

The procedure of Experiment 15 was repeated with inclusion of water (80 mg; 4.44×10$^{-3}$ mol, 12 weight %, based on diethylenetriamine). Glc analysis of the cooled reaction mixture indicated that a minor amount of reforming had occurred (see Table IV).

Experiment 17

A mixture of diethylenetriamine (670 mg; 6.5×10$^{-3}$ mol) and aluminum nitrate (61 mg; 1.625×10$^{-4}$ mol, 2.5 mol %, based on diethylenetriamine) was added to a two milliliter reactor. The aluminum nitrate contained water (26 mg; 1.46×10$^{-3}$ mol, 4.0 weight %, based on diethylenetriamine). This mixture was heated at 352° C. with agitation for 2 hours. Cooling and glc analysis indicated that some reforming to polyamines had occurred (see Table IV).

Experiment 18

A mixture of diethylenetriamine (670 mg; 6.5×10$^{-3}$ mol), aluminum nitrate (61 mg; 1.625×10$^{-4}$ mol, 2.5 mol %, based on diethylenetriamine) and water (80 mg; 4.44×10$^{-3}$ mol, 12 weight %, based on diethylenetriamine) was placed in a two milliliter reactor. The total incorporation of water with the aluminum nitrate catalyst (26 mg) and the feedstock (80 mg) was 106 mg (5.89×10$^{-3}$ mol; 16.0 weight %, based on diethylenetriamine). The resulting mixture was heated at 325° C. with agitation for 2 hours. Cooling and glc analysis of the product indicated that substantial reforming to polyamines had occurred (see Table IV).

These experiments demonstrate the beneficial effect of added water on reforming diethylenetriamine by nitrate catalysis.

Experiment 19

A mixture of diethylenetriamine (670 mg; 6.5×10$^{-3}$ mol) and anhydrous ammonium sulfate (43 mg; 3.25×10$^{-4}$ mol, 5.0 mol %, based on diethylenetriamine) was placed in a two milliliter reactor. The mixture was heated at 275° C. with agitation for 3 hours. Cooling and glc analysis of the product indicated that substantial reforming to a mixture of polyamines had occurred (see Table V).

Experiment 20

The procedure of Experiment 19 was repeated with inclusion of water (76 mg; 4.2×10$^{-3}$ mol, 11.3 weight %, based on diethylenetriamine). Glc analysis of the cooled reaction mixture indicated that substantial reforming to a mixture of polyamines had occurred, more than in Experiment 19, though with a lower proportion of non-cyclic products (see Table V).

Experiment 21

A mixture of diethylenetriamine (670 mg; 6.5×10$^{-3}$ mol) and beryllium sulfate (58 mg; 3.25×10$^{-4}$ mol, 5 mol %, based on diethylenetriamine) was placed in a two milliliter reactor. The beryllium sulfate also contained water (23 mg; 1.3×10$^{-3}$ mol, 3.5 weight %, based on diethylenetriamine) as water of crystallization. This mixture was heated at 275° C. with agitation for 3 hours. Cooling and glc analsis indicated that substantial reforming to mixture of polyamines had occurred (see Table V).

Experiment 22

The procedure of Experiment 21 was repeated with inclusion of additional water (76 mg; 4.2×10$^{-3}$ mol, 11.3 weight %, based on diethylenetriamine). Total incorporation of water with beryllium sulfate (3.5 weight %) and the feedstock (11.3 weight %) was 99 mg. (5.5×10$^{-3}$ mol, 14.8 weight %, based on diethylenetriamine). Glc analysis of the cooled reaction mixture indicated that substantial reforming to a mixture of polyamines had occurred, to a degree much greater than in Experiment 21 (see Table V).

These experiments illustrate the beneficial effect of water on reforming diethylenetriamine by sulfate catalysis.

TABLE IV

Reforming Diethylenetriamine With Nitrate Salts at 325° C.[a]

| Ex. | Catalyst Level (mol %) | Water (weight %) | EDA[b] | PIP[c] | AEP[d] | DETA[e] | TETA(L)[f] | TETA(C)[g] | TEPA(L)[h] | TEPA(C)[i] | NC[j] |
|---|---|---|---|---|---|---|---|---|---|---|---|
| 15 | 0.0 | 0.0 | 0.70 | 0.00 | 0.29 | * | 0.21 | 0.00 | 0.00 | 0.00 | 76 |
| 16 | 0.0 | 12.0 | 1.61 | 0.00 | 0.12 | * | 0.35 | 0.00 | 0.00 | 0.00 | 94 |
| 17 | 2.5 | 4.0 | 6.44 | 0.54 | 1.63 | * | 0.32 | 0.17 | 1.02 | 0.00 | 77 |
| 18 | 2.5 | 16.0 | 9.69 | 0.87 | 3.22 | * | 0.17 | 0.62 | 2.69 | 1.09 | 68 |

[a]Weight percent of components in product on feedstock-free basis. Catalyst and water incorporations are based on polyamine feedstock. Two hour reaction time, all cases.
[b]Ethylenediamine
[c]Piperazine
[d]Aminoethylpiperazine
[e]Diethylenetriamine
[f]Triethylenetetramine (linear isomers)
[g]Triethylenetetramine (cyclic isomers)
[h]Tetraethylenepentamine (linear isomers)
[h]Tetraethylenepentamine (linear isomers)
[i]Tetraethylenepentamine (cyclic isomers)
[j]Weight percent of non-cyclic products
*Feedstock

TABLE V

Reforming Diethylenetriamine With Sulfate Salts at 275° C.[a]

| Ex. | Catalyst Level (mol %) | Water (weight %) | EDA[b] | PIP[c] | AEP[d] | DETA[e] | TETA(L)[f] | TETA(C)[g] | TEPA(L)[h] | TEPA(C)[i] | NC[j] |
|---|---|---|---|---|---|---|---|---|---|---|---|
| 19 | 5.0 | 0.0 | 14.58 | 2.42 | 7.53 | * | 6.18 | 3.02 | 0.00 | 0.00 | 62 |
| 20 | 5.0 | 11.3 | 21.70 | 4.66 | 5.96 | * | 3.90 | 10.47 | 0.00 | 1.91 | 53 |

TABLE V-continued

Reforming Diethylenetriamine With Sulfate Salts at 275° C.[a]

| Ex. | Catalyst Level (mol %) | Water (weight %) | EDA[b] | PIP[c] | AEP[d] | DETA[e] | TETA(L)[f] | TETA(C)[g] | TEPA(L)[h] | TEPA(C)[i] | NC[j] |
|---|---|---|---|---|---|---|---|---|---|---|---|
| 21 | 5.0 | 3.5 | 13.55 | 5.28 | 1.36 | * | 7.11 | 5.81 | 5.61 | 0.00 | 68 |
| 22 | 5.0 | 14.8 | 25.16 | 9.17 | 0.85 | * | 4.48 | 16.10 | 0.00 | 2.24 | 51 |

[a]Weight percent of components in product on feedstock-free basis. Catalyst and water incorporations are based on polyamine feedstock. Reaction time three hours, all cases.
[b]Ethylenediamine
[c]Piperazine
[d]Aminoethylpiperazine
[e]Diethylenetriamine
[f]Triethylenetetramine (linear isomers)
[g]Triethylenetetramine (cyclic isomers)
[h]Tetraethylenepentamine (linear isomers)
[i]Tetraethylenepentamine (cyclic isomers)
[j]Weight percent of non-cyclic products
*Feedstock By way of generalization, the foregoing demonstrates the process of the present invention, wherein polyalkylene polyamines are reformed into other polyalkylene polyamines, preferably non-cyclic products, by reaction at elevated temperature and pressure with water and with metal sulfate or nitrate catalysts. Of particular interest are those experiments in which, under otherwise identical experimental conditions, the process is compared utilizing different catalysts or different amounts of water or different temperatures. As to catalysts, it will be noted that examples have been presented of processes utilizing beryllium sulfate, ammonium sulfate, ferric nitrate, beryllium nitrate and aluminum nitrate. However, these are considered representative of a much larger group of metals that may be used including the sulfate and nitrate groups set forth above.

More generally, while this invention has been described with respect to specific embodiments thereof, it is not limited thereto and the appended claims are intended to be construed to include not only the specific embodiments described or referred to, but to such other embodiments of the invention as may be devised by those skilled in the art.

INDUSTRIAL APPLICATION OF THE INVENTION

This invention may be used to produce polyalkylene polyamine reactants having a variety of industrial applications, and particularly to produce from other lower molecular weight polyalkylene polyamines, higher, non-cyclic polyalkylene polyamines, which are of enhanced commercial value.

We claim:

1. A method for reforming a feedstock of ethylene diamine or polyalkylene polyamine into a polyalkylene polyamine product different from said feedstock, said method comprising heating said feedstock with water and a catalyst to a temperature of 200°–400° C., in a reaction vessel, said catalyst comprised of a metal salt from the group consisting of ammonium sulfate and a sulfate or nitrate of lithium, sodium, potassium, and other metals of group IA of the periodic table; beryllium, magnesium, calcium, and other metals of group IIA of the periodic table; aluminum, zinc, zirconium, antimony, tin (valence states II and IV) and iron (valence states II and III), said method comprising holding said feedstock with water and catalyst at said temperature for 0.5–4 hours, said proportion of catalyst and water with said feedstock, said feedstock temperature and said time of heating all being selected to cause conversion of said feedstock to a different polyalkylene polyamine product.

2. A method, as recited in claim 1, wherein said polyamine of said feedstock is a compound selected from the group consisting of diethylene triamine and triethylene tetramine.

3. A method, as recited in claim 1, wherein said feedstock, water and catalyst are heated to 225°–350° C.

4. A method, as recited in claim 3, wherein said feedstock, water and catalyst are heated for 1 to 4 hours.

5. A method, as recited in claim 4, wherein said feedstock is a compound selected from the group consisting of ethylene diamine, diethylene triamine and triethylene tetramine.

6. A method, as recited in claim 1 or claim 5, wherein said catalyst is present in an amount of 5–8 mol percent based on the feedstock.

7. A method, as recited in claim 1 or claim 5, said catalyst being present in an amount of 1–10 mol percent based on the feedstock.

8. A method, as recited in any of claims 1 to 5, wherein said catalyst is $(NH_4)_2SO_4$.

9. A method, as recited in claim 6, wherin said catalyst is beryllium sulfate.

* * * * *